US00PP26519P2

(12) United States Plant Patent
Heuger

(10) Patent No.: US PP26,519 P2
(45) Date of Patent: Mar. 15, 2016

(54) ***HELLEBORUS* PLANT NAMED 'COSEH 1080'**

(50) Latin Name: *Helleborus hybrida*
Varietal Denomination: COSEH 1080

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 188 days.

(21) Appl. No.: 13/999,072

(22) Filed: Jan. 10, 2014

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 1080', characterized by its upright and mounding plant habit; uniform and freely flowering habit; solid green-colored leaves; freely flowering habit; single pink and green-colored flowers; and good garden performance.

2 Drawing Sheets

Botanical designation: *Helleborus hybrida.*
Cultivar denomination: 'COSEH 1080'.

BACKGROUND OF THE INVENTION

The present invention relates to a new and distinct cultivar of *Helleborus* plant, botanically known as *Helleborus hybrida* and hereinafter referred to by the name 'COSEH 1080'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in January, 2007 of an unnamed proprietary seedling selection of *Helleborus niger,* not patented, as the female, or seed, parent with an unnamed proprietary seedling selection of *Helleborus hybrida,* not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2010.

Asexual reproduction of the new *Helleborus* plant by divisions in a controlled greenhouse environment in Glandorf, Germany since March, 2010 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 1080'. These characteristics in combination distinguish 'COSEH 1080' as a new and distinct *Helleborus* plant:

1. Upright and mounding plant habit.
2. Uniform and freely flowering habit.
3. Solid green-colored leaves.
4. Freely flowering habit.
5. Single pink and green-colored flowers.
6. Good garden performance.

Compared to plants of the parent selections, plants of the new *Helleborus* are more uniformly mounded and are more freely flowering.

Plants of the new *Helleborus* can be compared to plants of *Helleborus×nigercors* 'COSEH 750', disclosed in U.S. Plant Pat. No. 22,018. In side-by-side comparisons conducted in Glandorf, Germany, plants of the new *Helleborus* differed primarily from plants of 'COSEH 750' in the following characteristics:

1. Leaves of plants of the new *Helleborus* were lighter green in color than leaves of plants of 'COSEH 750'.
2. Plants of the new *Helleborus* and 'COSEH 750' differed in flower color as plants of 'COSEH 750' had light green to white-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 1080' grown in a container.

The photograph on the second sheet is a close-up view of a typical flower and flower bud of 'COSEH 1080'.

DETAILED BOTANICAL DESCRIPTION

The aforementioned photographs and following observations, measurements and values describe plants grown during the autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus hybrida* 'COSEH 1080'.

Parentage:

*Female, or seed, parent*.—Unnamed proprietary seedling selection of *Helleborus niger,* not patented.

*Male, or pollen, parent*.—Unnamed proprietary seedling selection of *Helleborus hybrida,* not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; low vigor to moderately vigorous growth habit.

*Plant height, soil level to top of foliar plane*.—About 18 cm.

*Plant height, soil level to top of flowers*.—About 21.9 cm.

*Plant diameter* (*area of spread*).—About 35.5 cm.

Leaf description:

*Arrangement*.—Leaves arranged in a basal rosette; leaves palmately compound with five or occasionally seven leaflets per leaf.

*Leaf length*.—About 16.6 cm.

*Leaf width*.—About 20.4 cm.

*Leaflet length*.—About 10.7 cm.

*Leaflet width*.—About 6 cm.

*Leaf shape*.—Palmate; orbicular to reniform in outline.

*Leaflet shape*.—Obovate to narrowly obovate.

*Leaflet apex*.—Acute.

*Leaflet base*.—Attenuate.

*Leaflet margin*.—Serrate.

*Leaflet texture, upper and lower surfaces*.—Smooth, glabrous; leathery.

*Leaflet luster, upper and lower surfaces*.—Slightly glossy.

*Leaflet venation pattern*.—Pinnate.

*Leaflet color*.—Developing leaves, upper surface: Close to 137A. Developing leaves, lower surface: Close to 147B. Fully developed leaves, upper surface: Close to N137A to N137C; venation, close to 144A to 144B. Fully developed leaves, lower surface: Close to 147B; venation, close to 145A.

*Petioles*.—Length: About 10.3 cm. Diameter: About 4.5 mm to 5.5 mm. Texture, upper and lower surfaces: Smooth, glabrous. Color, upper and lower surfaces: Close to 144A.

Flower description:

*Flower shape and habit*.—Single rotate flowers arranged singly or in pairs; freely and uniform flowering habit with about five flowers developing per plant; flowers facing mostly outwardly to slightly nodding.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Flower buds*.—Length: About 2.6 cm. Diameter: About 1.3 cm. Shape: Ovate. Color: Close to 158D strongly tinged with close to 182D; towards the apex, close to 183D.

*Flower diameter*.—About 9.2 cm.

*Flower depth* (*height*).—About 2.5 cm.

*Petals*.—Transformed into nectaries.

*Sepals*.—Quantity and arrangement: Five, arranged in a single whorl. Length: About 5.5 cm. Width: About 4.5 cm. Shape: Ovate to broadly ovate; concave. Apex: Bluntly acute to obtuse. Base: Broadly cuneate. Margin: Entire. Texture, upper and lower surfaces: Smooth, glabrous. Color: When opening, upper surface: Close to NN155D moderately to strongly tinged with close to 63D and 70C; towards the apex and the base, close to 145A to 145B. When opening, lower surface: Close to NN155D moderately to strongly tinged with close to 70C and 70D; venation, close to 61A; towards the apex and the base, close to 144A. Fully opened, upper surface: Close to 145C tinged with close to 70C; towards the base, close to 145B. Fully opened, lower surface: Close to 145C strongly tinged with close to 70C and 185C.

*Peduncles*.—Length: About 14 cm. Diameter: About 6.5 mm to 8 mm. Aspect: About 5° from vertical. Strength: Moderately strong. Texture: Smooth, glabrous. Color: Close to 144B to 144C; basally and distally, moderately tinged with close to 187D.

*Pedicels*.—Length: About 4.5 cm. Diameter: About 4 mm. Aspect: About 30° from peduncle axis. Strength: Moderately strong. Texture: Smooth, glabrous. Color: Close to 144B moderately speckled with close to 187C.

*Reproductive organs*.—Stamens: Quantity per flower: About 120. Filament length: About 1.6 cm. Filament color: Close to NN155D. Anther shape: Reniform; basifixed. Anther length: About 2.5 mm. Anther color: Close to 150C. Pollen amount: Moderate. Pollen color: Close to 4D. Pistils: Quantity per flower: About five to seven. Pistil length: About 8 mm. Stigma shape: Club-shaped. Stigma color: Close to 155A. Style length: About 7.5 mm. Style color: Close to 184B. Ovary color: Close to 150D. Nectaries (transformed petals): Quantity per flower: About 15. Length: About 1 cm. Diameter: About 5 mm. Shape: Tubular, flattened. Color, immature, inner and outer surfaces: Close to 145D; towards the base, close to 144C and 145A. Color, mature, inner and outer surfaces: Close to 153C to 153D; towards the base, close to N144A.

*Seeds and fruits*.—Seed and fruit development have not been observed on plants of the new *Helleborus.*

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 1080' as illustrated and described.

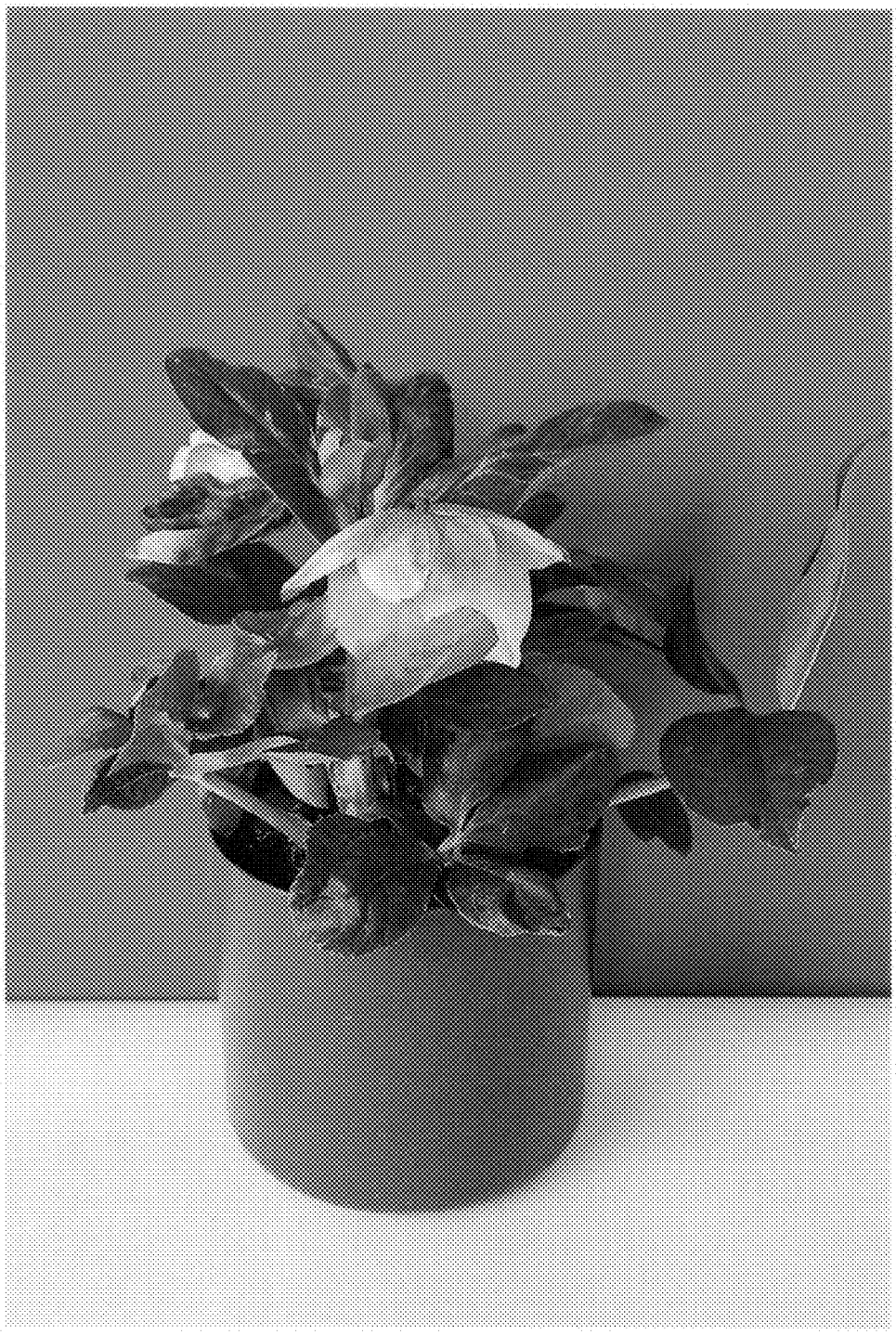

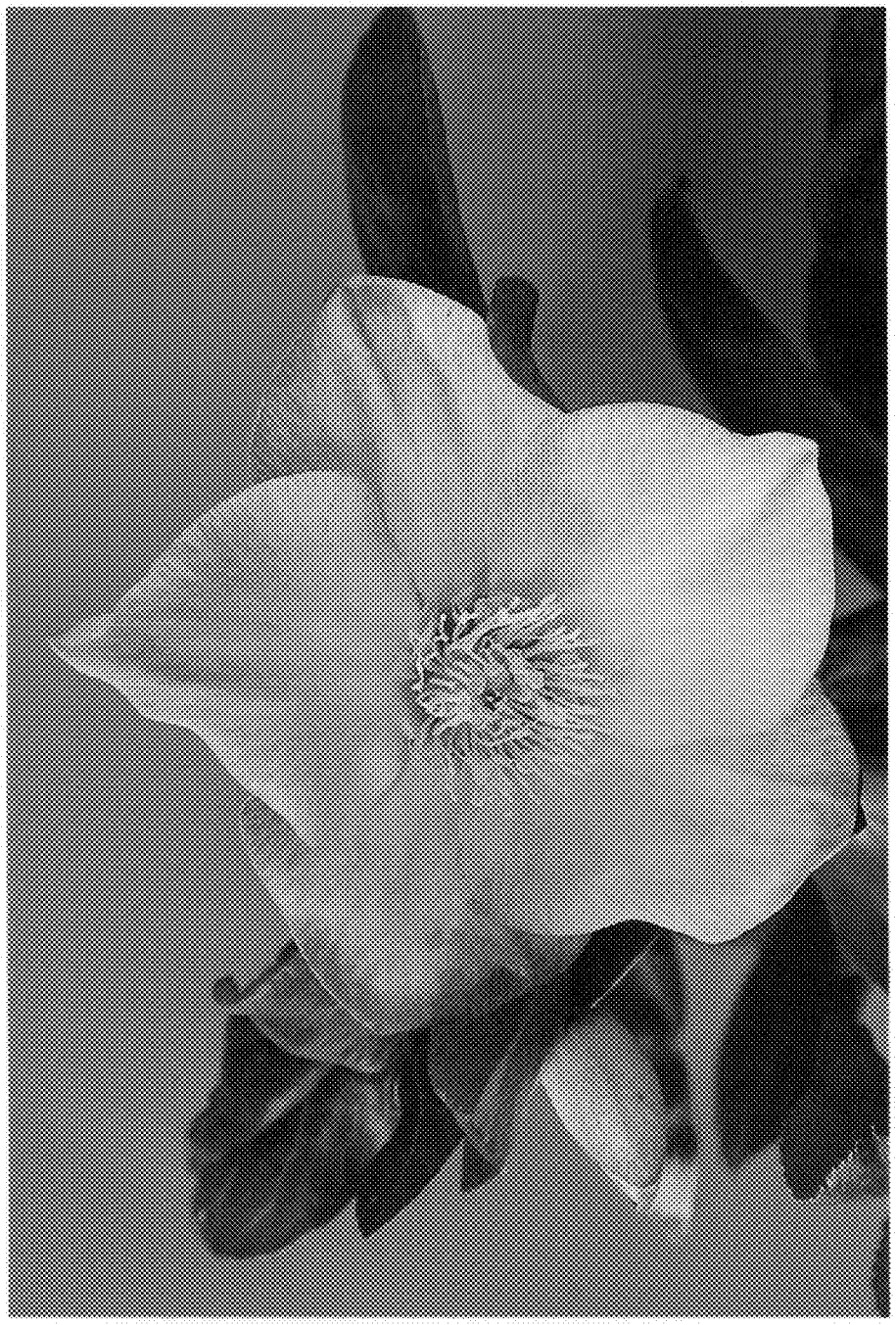

* * * * *